United States Patent [19]

Matsubara et al.

[11] Patent Number: 5,055,585

[45] Date of Patent: Oct. 8, 1991

[54] PREPARATION PROCESS OF AMINOKETONES

[75] Inventors: Akira Matsubara, Yokohama; Kazuya Sakai, Mobara; Hideki Tanada, Mobara; Hironori Komatsu, Mobara, all of Japan

[73] Assignee: Mitsui Toatsu Chemicals, Incorporated, Tokyo, Japan

[21] Appl. No.: 647,633

[22] Filed: Jan. 31, 1991

[30] Foreign Application Priority Data

Feb. 8, 1990 [JP] Japan .................................. 2-27119

[51] Int. Cl.$^5$ .................. C07D 275/04; C07D 261/20; C07D 275/02; C07D 61/29

[52] U.S. Cl. ................................... 548/248; 548/207; 548/214; 548/241; 546/270; 546/275; 546/280; 568/332; 568/404

[58] Field of Search ............... 548/241, 248, 207, 214; 568/332, 404; 546/270, 275, 280

Primary Examiner—Mary C. Lee
Assistant Examiner—Joseph K. McKane
Attorney, Agent, or Firm—Nixon & Vanderhye

[57] ABSTRACT

Novel aminoketones useful as central muscle relaxants and their preparation processes are disclosed. The disclosed processes are novel processes which do not use any heavy metal in view of the facts that their products are will be used as drugs and which require no complex purification step such as liberation of the aminoketones from their hydrochlorides or the like.

8 Claims, No Drawings

PREPARATION PROCESS OF AMINOKETONES

BACKGROUND OF THE INVENTION

1. Field of the Invention

The present invention relates to a process for the preparation of aminoketones useful as central muscle relaxants. This invention is also concerned with a process for the preparation of intermediates for the aminoketones.

More specifically, the present invention pertains to a process for preparing a compound of the following formula [VI]:

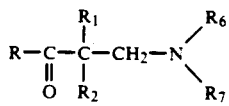

by oxidizing a compound of the following formula [I]:

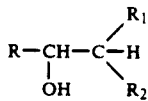

to obtain a compound of the following formula [IV]:

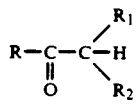

and then forming the compound of the formula [VI] from the compound of the formula [IV]. The substituents R, $R_1$, $R_2$, $R_6$ and $R_7$ will be defined herein. Compounds of the formula [VI] are novel compounds and are useful as central muscle relaxants.

2. Description of the Related Art

It is generally known to use a heavy metal such as chromic acid as an oxidizing agent upon preparation of a ketone from a secondary alcohol. Such heavy metals are however noxious from biological and other standpoints, so that their use in the production of pharmaceutical products is not preferred.

Some processes which use an oxidizing agent other than heavy metals have hence been proposed, including the process using sodium hypochlorite and a phase transfer catalyst in combination [Lee, G. A., et al., Tetrahedron Letters, 1641 (1976)] and the process in which calcium hypochlorite is used in the presence of an acidic solvent such as acetic acid [Nwavkwa, S. D., et al., Tetrahedron Letters, 35 (1982)]. These oxidizing processes were however unable to prepare a ketone of the formula [IV] from an alcohol of the formula [I].

As a still further process for preparing an aminoketone from a ketone, it has been known to react the ketone with paraformaldehyde and an amine hydrochloride in the presence of concentrated hydrochloric acid in an alcoholic solvent (Japanese Patent Application Laid-Open No. 119444/1988). In the aminoketone prepared by this process, the amine moiety is however in its hydrochloride form. It is therefore necessary to convert the reaction product to the free aminoketone by neutralizing it with a suitable alkali agent, for example, aqueous ammonia or an aqueous solution of sodium hydroxide. The above process hence cannot avoid inconvenience such as higher production cost and complicated production steps.

SUMMARY OF THE INVENTION

The present invention has been completed to overcome the problems described above.

In one aspect of the present invention, there is thus provided a process for the preparation of a ketone represented by the following formula [IV]:

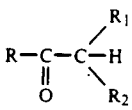

wherein R means

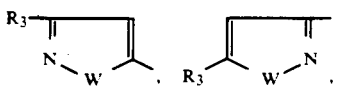

$R_3$ being a halogen atom, a lower alkyl group, a benzyl group, a benzoyl group, a pyridyl group, a furyl group which may be substituted by one or more lower alkyl groups, a thienyl group which may be substituted by one or more lower alkyl groups, a phenyl group which may be substituted by one or more halogen atoms or lower alkoxy, lower alkyl, trifluoromethyl, cyano, nitro, amino, dimethylamino, acetamido, methanesulfonylamido, acetyl or lower alkoxycarbonyl groups, or a naphthyl group, $R_4$ and $R_5$ independently representing a phenyl or lower alkyl group, and W standing for an oxygen or sulfur atom, $R_1$ denotes a hydrogen atom, a lower alkyl group, a benzyl group, a methoxy group, a phenyl group, an allyl group, a lower alkyl group substituted by one or more trifluoromethyl or lower alkoxy groups, or a cyclopropylmethyl group, and $R_2$ means a hydrogen atom or a lower alkyl group, or $R_1$ and $R_2$ being coupled together to form an alicyclic five- or six-membered ring, which comprises:

reacting an alcohol represented by the following formula [I]:

wherein R, $R_1$ and $R_2$ have the same meanings as defined above, in the presence of (i) a hypohalite represented by the following formula [II]:

$$M(O-X)_n \qquad [II]$$

wherein M means an alkali metal or alkaline earth metal, X denotes a halogen atom; and n stands for 1 when M is an alkali metal or 2 when M is an alkaline earth metal and (ii) a pyridine represented by the following formula [III]:

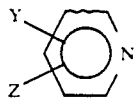 [III]

wherein Y and Z individually mean a hydrogen atom or a lower alkyl group, or an acid addition salt thereof.

In another aspect of the present invention, there is also provided a process for the preparation of a compound having excellent action as a central muscle relaxant, namely, an aminoketone represented by the following formula [VI]:

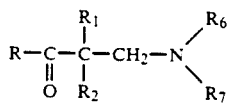 [VI]

wherein R, $R_1$ and $R_2$ have the same meanings as defined above; and $R_6$ and $R_7$ mean lower alkyl groups which may be the same or different, or $R_6$ and $R_7$ may be coupled together to form together with the adjacent nitrogen atom a five- to eight-membered ring which may have one or more branches, which comprises:

reacting an amine represented by the following formula [V]:

 [V]

wherein $R_6$ and $R_7$ have the same meanings as defined above, with the ketone represented by the [IV] in the presence of an aqueous solution of formaldehyde.

The above processes of the present invention are industrially advantageous for the preparation of the aminoketones [VI] which are extremely useful as central muscle relaxants.

Where the alcohol [I] as the starting material can be prepared by using the hypohalite [II], the reaction of the alcohol [I] to the ketone of the formula [IV] as the intermediate can be conducted in the same reactor without the need for the isolation of the alcohol [I] from the reaction mixture.

DETAILED DESCRIPTION OF THE PREFERRED EMBODIMENTS

The above processes of the present invention can be combined together to prepare the aminoketone [VI] from the alcohol [I]. This can be described by the following reaction scheme;

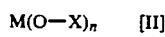 [II]

and

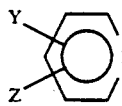 [III] or its acid addition salt

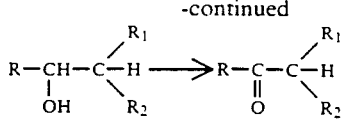 (1)

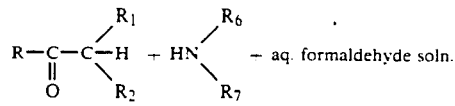

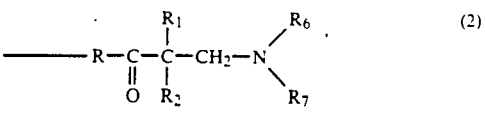 (2)

[VI]

wherein R, $R_1$, $R_2$, $R_6$ and $R_7$ have the same meanings as defined above.

Alcohol

The alcohol employed as a starting material in the above reaction scheme is, as already described above, represented by the following formula [I]:

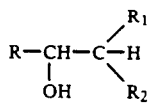 [I]

wherein R, $R_1$ and $R_2$ have the same meanings as defined above.

As the lower alkyl groups represented by $R_4$ and $R_5$, $C_{1-2}$ alkyl groups are preferred. Preferred examples of the lower alkyl group as $R_3$ include $C_{1-3}$ alkyl groups. The lower alkyl group of the substituted furyl or thienyl group as $R_3$ can preferably be a $C_{1-3}$ alkyl group. Exemplary alkoxy groups of the lower alkoxy or lower alkoxycarbonyl group in the substituted phenyl group as $R_3$ preferably include $C_{1-2}$ alkoxy groups. Preferred examples of the lower alkyl group in the substituted phenyl group as $R_3$ include $C_{1-2}$ alkyl groups.

Preferred examples of the lower alkyl group as $R_1$ include $C_{1-4}$ alkyl groups. The lower-alkoxy-substituted alkyl group as $R_1$ can preferably be a $C_{1-2}$ lower alkyl group substituted by a $C_{1-2}$ alkoxy group.

Further, the lower alkyl group as $R_2$ can preferably be a $C_{1-2}$ alkyl group.

Hypohalite

The hypohalite which is to be reacted with the alcohol [I] is represented by the following formula [II]:

 [II]

In the formula [II], M means an alkali metal or an alkaline earth metal. Illustrative of the alkali metal include lithium, sodium, potassium and cesium. Exemplary alkaline earth metals include magnesium, calcium, strontium and barium. Group X denotes a halogen atom, which may be a chlorine, bromine or iodine atom by way of example. n stands for 1 when M is an alkali metal and for 2 when M is an alkaline earth metal.

Pyridine or acid addition salt thereof

The pyridine is represented by the following formula [III]:

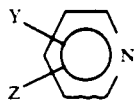

wherein Y and Z individually mean a hydrogen atom or a lower alkyl group.

Specific examples of the pyridine include:

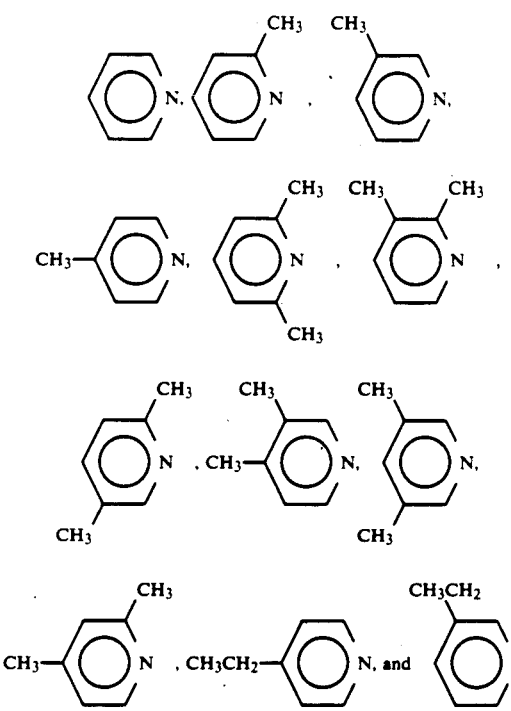

Further, illustrative of the acid addition salt of the pyridine [III] include addition salts with mineral acids such as hydrochloric acid, hydrobromic acid, nitric acid, sulfuric acid and phosphoric acid and also addition salts with organic acids such as methanesulfonic acid, benzenesulfonic acid, toluenesulfonic acid, acetic acid and propionic acid. One or more of these acid addition salts may be used to desired extent in combination with the pyridine [III].

Ketone

The ketone prepared from the alcohol [I] is represented by the following formula [IV]:

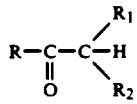

wherein R, $R_1$ and $R_2$ have the same meanings as defined above.

Amine

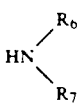

In the amine [V], $R_6$ and $R_7$ indicate the following two types of groups:

(1) $R_6$ and $R_7$ mean lower alkyl groups, which may be the same or different.

(2) $R_6$ and $R_7$ are coupled together to form together with the adjacent nitrogen atom a five- to eight-membered ring which may have one or more branches.

Illustrative of the lower alkyl groups in the type (1) include methyl, ethyl, isopropyl and butyl.

On the other hand, specific examples of the five- to eight-membered ring in the type (2) include:

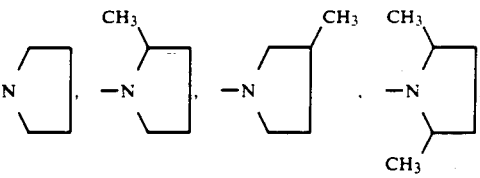

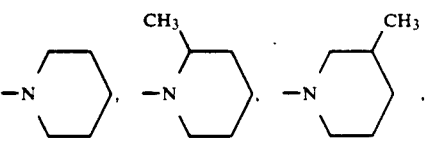

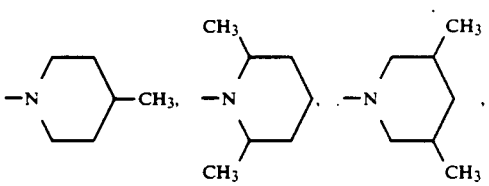

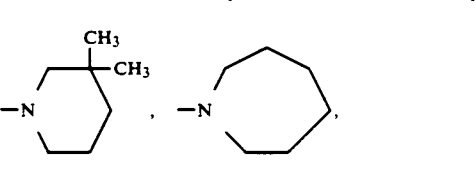

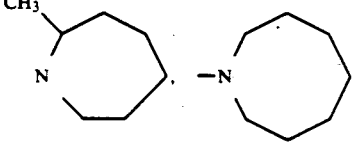

Synthetic reaction

According to the reaction scheme described above, the alcohol [I] is reacted in the presence of the hypohalite [II] and the pyridine [III] or the acid addition salt thereof to synthesize the ketone [IV]. The ketone [IV] is then reacted with the amine [V] in the presence of the aqueous solution of formaldehyde, thereby synthesizing the aminoketone [VI].

The above synthetic reaction is expressed by the reaction formulae (1) and (2) as is shown in the above reaction scheme.

In the reaction formula (1), the hypohalite [II] is used generally at a molar ratio of 0.5 to 20, preferably at a molar ratio of 1 to 5 relative to the alcohol [I] upon synthesis of the ketone [IV]. If necessary, the hypohalite [II] can be used as an aqueous solution and can be added, for example, dropwise to the reaction mixture.

The pyridine [III] or the acid addition salt thereof is used generally at a molar ratio of 0.01 to 10, preferably at a molar ratio of 0.1 to 5 relative to the alcohol [I].

If necessary, the pyridine [III] or the acid addition salt thereof can be used as a solution in water, an acidic aqueous solution such as acetic acid, hydrochloric acid, sulfuric acid or phosphoric acid; an alcohol solution such as methanol, ethanol or isopropanol; an ether such as dioxane; a halogenated hydrocarbon solution such as chloroform, dichloromethane, 1,2-dichloroethane or 1,1,2-trichloroethane; acetonitrile solution; dimethylformamide solution, and can be added, for example, dropwise to the reaction mixture.

Upon conducting the reaction, it is also possible to use a reaction solvent as needed. Exemplary reaction solvents include hydrocarbons such as hexane, pentane and cyclohexane; aromatic hydrocarbons such as benzene, toluene and xylene; alcohols such as methanol, ethanol and isopropanol; ethers such as tetrahydrofuran and dioxane; halogenated hydrocarbons such as chloroform, dichloromethane, carbon tetrachloride, 1,2-dichloroethane and 1,1,2-trichloroethane; esters such as methyl acetate, ethyl acetate and propyl acetate; water; acetonitrile; dimethylformamide; dimethylsulfoxide; and N-methyl-2-pyrrolidone.

The reaction can be carried out by stirring and mixing the alcohol [I], the hypohalite [II], and the pyridine [III] or the acid addition salt thereof at a temperature generally in a range of $-50°$ C. to $50°$ C., preferably in a range of $-30°$ C. to $40°$ C. for 0.5-48 hours in the absence of any solvent or in one or more of the above exemplified solvents.

After completion of the reaction, the target compound, i.e., the ketone [IV] can be isolated by a method commonly employed in the art, for example, by solvent extraction. A purification method known per se in the art, such as recrystallization or chromatography, can also be used as needed.

In the reaction formula (2) on the other hand, the amine [V] is used generally at a molar ratio of 0.5-5, preferably at a molar ratio of 1-2 relative to the ketone [IV] upon synthesis of the aminoketone [VI].

Further, the concentration of the aqueous solution of formaldehyde is generally 5-50%, preferably 10-40%. The aqueous solution of formaldehyde is used generally at a molar ratio of 0.5-5, preferably at a molar ratio 1-2 relative to the ketone [IV].

Upon reaction, it is possible to use a reaction solvent as needed. Illustrative of the reaction solvent include alcohols such as methanol, ethanol, isopropanol, propanol, butanol, amyl alcohol and isoamyl alcohol.

The reaction can be conducted by stirring and mixing the ketone [IV] in the presence of the amine [V] and the aqueous solution of formaldehyde at a temperature generally in a range of $-30°$ C. to $100°$ C., preferably in a range of $-10°$ C. to $60°$ C. for 0.5-24 hours in the absence of any solvent or in one or more of the above-exemplified solvents.

After completion of the reaction, the target compound, namely, the aminoketone [VI] can be isolated by a method commonly employed in the art, for example, by solvent extraction.

In addition, a purification method known per se in the art, such as recrystallization or chromatography, can also be used as needed.

The present invention will hereinafter be described in detail by the following examples.

REFERENTIAL EXAMPLE 1

Synthesis of 5-(1-hydroxypropyl)-3-phenylisoxazole (Compound [I])

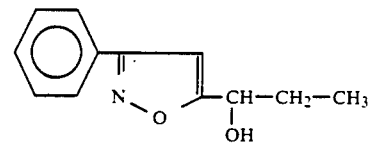

In 12.5 ml of dichloromethane, were dissolved 2.5 g (20.7 mmol) of benzaldoxime and 2.1 g (25.0 mmol) of 1-pentyne-3-ol. Under ice cooling, 14.5 g of a 12.0% aqueous solution of sodium hypochlorite were added dropwise addition, they were reacted at room temperature for 3 hours, followed by the extraction of the organic layer with dichloromethane. The extract was washed with water and the resulting organic layer was dried over anhydrous sodium sulfate. The solvent was distilled off under reduced pressure and the residue was purified by chromatography on a silica gel column (eluent: chloroform), whereby the target compound, namely, 5-(1-hydroxypropyl)-3-phenylisooxazole was obtained as crystals.

Yield: 3.3 g (78.7%).
Melting point: $101°-102°$ C.
NMR ($\delta$ ppm, $CDCl_3$): 1.0(3H,t,J=8 Hz), 1.6-2.2(2H,m), 3.1(1H,bs), 4.9(1H,t,J=6 Hz), 6.5(1H,s), 7.3-7.6(3H,m), 7.7-7.9(2H,m).

REFERENTIAL EXAMPLE 2

Synthesis of 5-(1-hydroxybutyl)-3-phenylisoxazole (Compound [I])

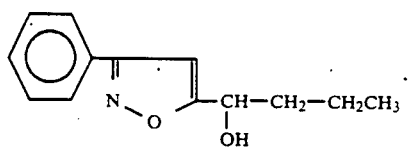

In 25 ml of dichloromethane, were dissolved 5.0 g (41.3 mmol) of benzaldoxime and 4.5 g (45.9 mmol) of 1-hexyne-3-ol. Under ice cooling, 29.0 g of a 12.0% aqueous solution of sodium hypochlorite were added dropwise to the solution over 30 minutes. After completion of the dropwise addition, they were reacted at $20°$ C. for 2 hours. After completion of the reaction, the reaction mixture was extracted with dichloromethane and the organic layer was washed with water. The organic layer was dried over anhydrous sodium sulfate and the solvent was then distilled off under reduced pressure. The residue was purified by chromatography on a silica gel column (eluent: chloroform), whereby the target compound, namely, 5-(1-hydroxybutyl)-3-phenylisooxazole was obtained as an oil.

Yield: 6.5 g (72.5%)
NMR ($\delta$ ppm, $CDCl_3$): 0.7-1.1(3H,m), 1.1-2.1(4H,m), 3.8(1H,m), 4.8(1H,t,J=7 Hz), 6.4(1H,s), 7.2-7.5(3H,m), 7.5-7.9(2H,m).

EXAMPLE 1

Synthesis of 5-propionyl-3-phenylisoxazole (Compound [IV])

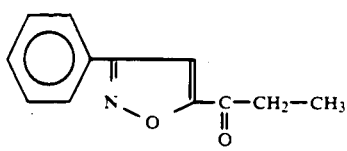

In 10 ml of dichloromethane, 1.0 g (5.0 mmol) of 5-(1-hydroxypropyl)-3-phenylisoxazole was dissolved. To the solution were added 100 mg (0.9 mmol) of pyridine hydrochloride, followed by the further addition of 1.4 g (9.9 mmol) of calcium hypochlorite. They were reacted at room temperature for 5 hours. After completion of the reaction, insoluble matter was filtered off and the organic layer was washed with water. The organic layer was dried over anhydrous sodium sulfate and the solvent was distilled off under reduced pressure. The residue was then recrystallized from ethanol, whereby the target compound, namely, 5-propionyl-3-phenylisoxazole was obtained as crystals.

Yield: 0.9 g (91.0%).
Melting point: 111°-112° C.
NMR (δ ppm, CDCl$_3$): 1.3(3H,t,J=8 Hz), 3.1(2H,q,J=8 Hz), 7.2(3H,s), 7.5-8.0(5H,m).

EXAMPLE 2-1

Synthesis of 5-butyryl-3-phenylisoxazole (Compound [IV])

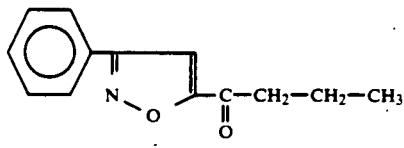

In 12.5 ml of dichloromethane, 4.4 g (20 mmol) of 5-(1-hydroxybutyl)-3-phenylisoxazole were dissolved. While the solution was being stirred, 35.2 g (60 mmol) of a 12.7% aqueous solution of sodium hypochlorite were added dropwise to the solution. Next, a liquid mixture which had been obtained by adding 0.48 g (6.1 mmol) of pyridine to 1.0 ml of 6N hydrochloric acid) was added dropwise over 1 hour and the reaction temperature was maintained at 20° C. After completion of the reaction, the organic layer was collected and was washed successively with a 5% aqueous solution of sodium hydrogensulfite, water and 1N hydrochloric acid. The organic layer was dried over anhydrous sodium sulfate and the solvent was distilled off under reduced pressure. The residue was then recrystallized from ethanol, whereby the target compound, namely, 5-butyryl-3-phenylisoxazole was obtained as crystals.

Yield: 2.9 g (66.5%).
Melting point: 89°-90° C.
NMR (δ ppm, CDCl$_3$): 1.0(3H,t,J=7 Hz), 1.5-2.1(2H,m), 2.0(2H,t,J=7 Hz), 7.2(1H,s), 7.3-7.6(3H,m), 7.6-8.0(2H,m).

EXAMPLE 2-2

Synthesis of 5-butyryl-3-phenylisoxazole (Compound [IV])

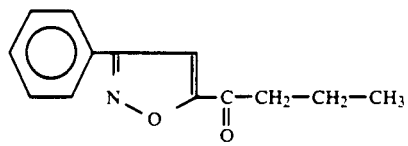

In 12.5 ml of dichloromethane, were dissolved 2.5 g (20.6 mmol) of benzaldoxime and 2.3 g (22.9 mmol) of 1-hexyne-3-ol. Under ice cooling, 15.6 g of a 12% aqueous solution of NaOCl were added dropwise to the solution while the reaction temperature was controlled at 5° C. The reaction mixture was then stirred at room temperature for 3 hours so that a reaction mixture of 5-(1-hydroxybutyl)-3-phenylisoxazole was obtained.

The reaction mixture was added with 39.0 g of a 12% aqueous solution of NaOCl, followed by the dropwise addition of 0.7 g (6.1 mmol) of pyridine hydrochloride in 3 ml of water while the reaction mixture was maintained at 15°-20° C. They were reacted for additional 1 hour at the same temperature. After completion of the reaction, the organic layer was separated and then washed successively with a 5% aqueous solution of sodium hydrogensulfite, water and 1N hydrochloric acid. The organic layer was dried over anhydrous sodium sulfate and the solvent was distilled off under reduced pressure. The residue was recrystallized from ethanol, whereby the target compound, namely, 5-butyryl-3-phenylisoxazole was obtained as crystals.

Yield: 2.8 g (63.7%).
The melting point and NMR data were consistent with those of the same compound synthesized in Example 2-1.

EXAMPLES 3-5

The target compounds [IV], namely, the ketones shown in Table 1 were obtained by conducting similar reactions to that of Examples 2-1 except for the use of the corresponding alcohols given in Table 1.

TABLE 1

| Ex. | Alcohol | Yield (%) | m.p. (°C.) | Target substance |
|---|---|---|---|---|
| 3 | (5-(1-hydroxy-2-methylpropyl)-3-phenylisoxazole structure) | 77 | 62-64 | (5-(2-methylpropanoyl)-3-phenylisoxazole structure) |

TABLE 1-continued

| Ex. | Alcohol | Yield (%) | m.p. (°C.) | Target substance |
|---|---|---|---|---|
| 4 | ![structure] phenyl-isoxazole-CH(OH)-CH₂CH₂CH₂CH₃ | 82 | 73-75 | ![structure] phenyl-isoxazole-C(=O)-CH₂CH₂CH₂CH₃ |
| 5 | ![structure] phenyl-isoxazole-CH(OH)-CH₂CH₂CH₂CH₂CH₃ | 80 | 83-85 | ![structure] phenyl-isoxazole-C(=O)-CH₂CH₂CH₂CH₂CH₃ |

EXAMPLE 6

Synthesis of 5-(2-piperidinomethylpropionyl)-3-phenylisoxazole (Compound [VI])

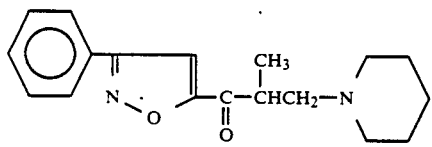

Added to 10 ml of ethyl alcohol were 2.0 g (10.0 mmol) of 5-propionyl-3-phenylisoxazole and 1.7 g (20.0 mmol) of piperidine, followed by the dropwise addition of 1.63 ml (20.0 mmol) of a 37% aqueous solution of formaldehyde under ice cooling. After the reaction mixture was stirred for 2 hours at room temperature, the solvent was distilled off under reduced pressure. The residue was dissolved in ethyl ether. The organic layer was washed with water and then dried over anhydrous sodium sulfate. The solvent was distilled off under reduced pressure, whereby the target compound, namely, 5-(2-piperidinomethylpropionyl)-3-phenylisoxazole was obtained as crystals.

Yield: 2.3 g (78%).
Melting point: 114°-116° C.
NMR (δ ppm, CDCl₃): 1.3(3H,d,J=6 Hz), 1.5-1.8(6H,m), 2.3-3.0(6H,m), 3.5-4.0(1H,m), 7.2(1H,s), 7.5-7.7(3H,m), 7.7-8.0(2H,m).

EXAMPLE 7

Synthesis of 5-(2-pyrrolidinomethylbutyryl)-3-phenylisoxazole (Compound [VI])

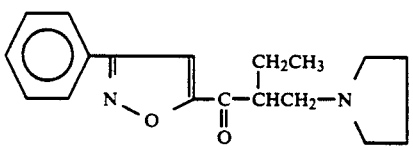

Added to 400 ml of ethyl alcohol were 200 g (0.93 mol) of 5-(2-pyrrolidinomethylbutyryl)-3-phenylisoxazole and 110 ml (1.32 mol) of pyrrolidine, followed by the dropwise addition of 120 ml (1.48 mol) of a 37% aqueous solution of formaldehyde under ice cooling over 30 minutes. After the reaction mixture was stirred for 1.5 hours at room temperature, the reaction mixture was concentrated to dryness under reduced pressure. The residue was dissolved in 1 l of ethyl ether. The resultant solution was washed with water and the organic layer then dried over anhydrous magnesium sulfate. The solvent was distilled off, whereby 5-(2-pyrrolidinomethylbutyryl)-3-phenylisoxazole was obtained as colorless crystals.

Yield: 264 g (95.2%).
Melting point: 68°-69° C.
NMR (δ ppm, CDCl₃): 0.9(3H,t,J=7 Hz), 1.3-2.0(6H,m), 7.2(1H,s), 7.2-7.6(3H,m), 7.6-8.0(2H,m).

EXAMPLE 8

Synthesis of 5-(2-piperidinomethylbutyryl)-3-phenylisoxazole (Compound [VI])

Added to 320 ml of ethyl alcohol were 160 g (0.74 mol) of 5-butyryl-3-phenylisoxazole and 103 ml of piperidine, followed by the dropwise addition of 96 ml (1.18 mol) of a 37% aqueous solution of formaldehyde under ice cooling over 30 minutes. After the reaction mixture was stirred for 1.5 hours at room temperature, the solvent was distilled off. The residue was dissolved in 800 ml of ethyl ether. The resultant solution was washed with water and the organic layer then dried over anhydrous magnesium sulfate. The solvent was distilled off, whereby the target compound, 5-(2-piperidinomethylbutyryl)-3-phenylisoxazole was obtained as colorless crystals.

Yield: 223 g (96.0%).
Melting point: 83°-84° C.
NMR (δ ppm, CDCl₃): 0.8-1.1(3H,m), 1.2-2.0(8H,m), 3.4-3.8(1H,m), 7.1(1H,s), 7.3-7.6(3H,m), 7.6-8.0(2H,m).

EXAMPLES 9-16

In Examples 9-12, the respective aminoketones shown in Table 2 were obtained in a similar manner to Example 6 except that amines

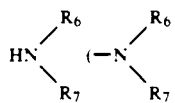

corresponding to those shown in Table 2) were used for the introduction of the group

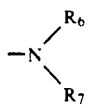

in place of piperidine.

In Example 13, the aminoketone shown in Table 2 was obtained in a similar manner to Example 7 except for the use of 2-methylpyrrolidine in lieu of pyrrolidine.

In Examples 14–16, the respective aminoketones given in Table 2 were obtained in a similar manner to Example 7 except that the ketones synthesized in Examples 3 and 4 were used, respectively instead of 5-butyryl-3-phenylisoxazole.

Analytical results of the individual aminoketones [VI] thus obtained are summarized in Table 2.

TABLE 2

| Ex. | $-R_8$ | $-N\begin{smallmatrix}R_6\\R_7\end{smallmatrix}$ | m.p. (°C.) | NMR(δ ppm, CDCl$_3$) |
|---|---|---|---|---|
| 9 | $-CH_3$ | $-N(CH_2CH_3)_2$ | 56–58 | 1.0(6H,t,J=7Hz) 1.1(3H,d,J=7Hz) 2.3–3.2(6H,m) 3.3–4.0(1H,m) 7.3(1H,s) 7.3–8.1(5H,m) |
| 10 | $-CH_3$ | pyrrolidine | Oil | 1.3(3H,d,J=7Hz) 1.5–2.0(4H,m) 2.3–2.8(5H,m) 3.0(1H,dd,J=12Hz, 8Hz) 3.2–3.9(1H,m) 7.2(1H,s) 7.3–7.6(3H,m) 7.6–7.9(2H,m) |
| 11 | $-CH_3$ | 2-methylpiperidine | 67–68 | 1.0–1.1(3H,m) 1.1–1.4(3H,m) 1.4–1.7(6H,m) 1.9–2.1(1H,m) 2.2–2.4(2H,m) 2.6–2.8(1H,m) 2.9–3.1(1H,m) 3.2–3.3(1H,dd,J=12Hz,8Hz) 3.6–3.8(1H,m) 7.2(1H,s) 7.3–7.5(3H,m) 7.7–7.9(2H,m) |
| 12 | $-CH_3$ | hexamethyleneimine | Oil | 1.2(3H,d,J=6Hz) 1.3–1.9(8H,m) 2.5–3.1(6H,m) 3.4–4.9(1H,m) 7.1(1H,s) 7.2–7.5(3H,m) 7.5–7.8(2H,m) |
| 13 | $-CH_2CH_3$ | 2-methylpyrrolidine | Oil | 0.8–3.7(18H,m) 7.3(1H,s) 7.3–7.6(3H,m) 7.6–8.0(2H,m) |
| 14 | $-CHCH_3$<br>$\mid$<br>$CH_3$ | pyrrolidine | 77–79 | 0.9–1.1(6H,m) 1.2–2.8(10H,m) 3.0–3.6(2H,m) 7.2(1H,s) 7.3–7.6(3H,m) 7.6–8.0(2H,m) |
| 15 | $-CH_2CH_2CH_3$ | pyrrolidine | 59–60 | 0.8–2.0(11H,m) 2.1–2.9(5H,m) 3.0(1H,dd,J=12Hz,8Hz) 3.3–3.8(1H,m) 7.2(1H,s) 7.3–7.7(3H,m) 7.7–8.0(2H,m) |

TABLE 2-continued

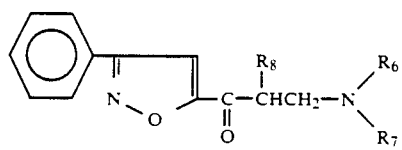

| Ex. | —R$_8$ | —N(R$_6$)(R$_7$) | m.p. (°C.) | NMR(δ ppm, CDCl$_3$) |
|---|---|---|---|---|
| 16 | —CH$_2$CH$_2$CH$_2$CH$_3$ | 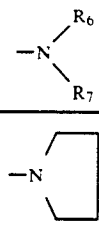 | 58–61 | 0.9(3H,t,J=7Hz) 1.2–1.3(4H,m) 1.5–2.0(6H,m) 2.4–2.6(5H,m) 3.0–3.1(1H,m) 3.06–3.7(1H,m) 7.2(1H,s) 7.4–7.5(3H,m) 7.8–7.9(2H,m) |

We claim:

1. A process for the preparation of a ketone represented by the following formula [IV]:

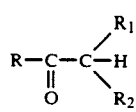   [IV]

wherein R means

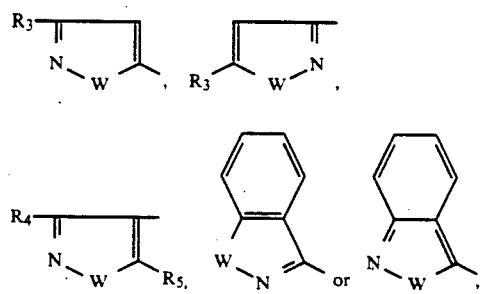

R$_3$ being a halogen atom, a lower alkyl group, a benzyl group, a benzoyl group, a pyridyl group, a furyl group which may be substituted by one or more lower alkyl groups, a thienyl group which may be substituted by one or more lower alkyl groups, a phenyl group which may be substituted by one or more halogen atoms or lower alkoxy, lower alkyl, trifluoromethyl, cyano, nitro, amino, dimethylamino, acetamido, methanesulfonylamido, acetyl or lower alkoxycarbonyl groups, or a naphthyl group, R$_4$ and R$_5$ independently representing a phenyl or lower alkyl group, and W standing for an oxygen or sulfur atom, R$_1$ denotes a hydrogen atom, a lower alkyl group, a benzyl group, a methoxy group, a phenyl group, an allyl group, a lower alkyl group substituted by one or more trifluoromethyl or lower alkoxy groups, or a cyclopropylmethyl group, and R$_2$ means a halogen atom or a lower alkyl group, or R$_1$ and R$_2$ being coupled together to form an alicyclic five- or six-membered ring, which comprises:

reacting an alcohol represented by the following formula [I]:

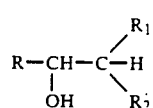   [I]

wherein R, R$_1$ and R$_2$ have the same meanings as defined above, in the presence of (i) a hypohalite represented by the following formula [II]:

M(O—X)$_n$   [II]

wherein M means an alkali metal or alkaline earth metal, X denotes a halogen atom, and n stands for 1 when M is an alkali metal or 2 when M is an alkaline earth metal and (ii) a pyridine represented by the following formula [III]:

   [III]

wherein Y and Z individually mean a hydrogen atom or a lower alkyl group, or an acid addition salt thereof.

2. The process of claim 1, wherein R is

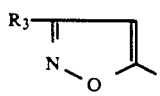

3. The process of claim 2, wherein R$_3$ is a phenyl group.

4. The process of claim 3, wherein R$_1$ is a hydrogen atom and R$_2$ is a lower alkyl group.

5. The process of claim 1, wherein the hypohalite is sodium hypochlorite.

6. The process of claim 1, wherein the pyridine of the formula [III] or the acid addition salt thereof is pyridine or pyridine hydrochloride.

7. The process of claim 1, wherein the hypohalite of the formula [II] is used at a molar ratio of 1–5 relative to the alcohol of the formula [I].

8. The process of claim 1, wherein the pyridine of the formula [III] or the acid addition salt thereof is used at a molar ratio of 0.1–5 relative to the alcohol of the formula [I].

* * * * *